(12) United States Patent
Yared

(10) Patent No.: US 9,724,172 B2
(45) Date of Patent: Aug. 8, 2017

(54) ENDODONTIC TOOL AND METHOD

(71) Applicant: Ghassan Yared, Toronto (CA)

(72) Inventor: Ghassan Yared, Toronto (CA)

( * ) Notice: Subject to any disclaimer, the term of this patent is extended or adjusted under 35 U.S.C. 154(b) by 0 days.

(21) Appl. No.: 14/426,645

(22) PCT Filed: Sep. 5, 2013

(86) PCT No.: PCT/CA2013/000757
§ 371 (c)(1),
(2) Date: Mar. 6, 2015

(87) PCT Pub. No.: WO2014/036634
PCT Pub. Date: Mar. 13, 2014

(65) Prior Publication Data
US 2015/0216623 A1    Aug. 6, 2015

(30) Foreign Application Priority Data
Sep. 7, 2012    (CA) ...................................... 2788880

(51) Int. Cl.
| | | |
|---|---|---|
| *A61C 1/00* | (2006.01) | |
| *A61C 1/18* | (2006.01) | |
| *A61C 1/08* | (2006.01) | |
| *A61C 1/12* | (2006.01) | |
| *A61C 1/14* | (2006.01) | |
| *A61C 5/40* | (2017.01) | |
| *A61C 5/42* | (2017.01) | |

(52) U.S. Cl.
CPC ............ *A61C 1/186* (2013.01); *A61C 1/0007* (2013.01); *A61C 1/08* (2013.01); *A61C 1/12* (2013.01); *A61C 1/14* (2013.01); *A61C 5/40* (2017.02); *A61C 5/42* (2017.02)

(58) Field of Classification Search
CPC ........... A61C 1/186; A61C 5/023; A61C 1/14; A61C 1/0007; A61C 1/08; A61C 1/12; A61C 5/02
See application file for complete search history.

(56) References Cited

U.S. PATENT DOCUMENTS

| | | | | |
|---|---|---|---|---|
| 6,955,536 B1 * | 10/2005 | Buchanan | ............ | A61C 1/0015 433/27 |
| 2015/0125807 A1 * | 5/2015 | Shipley | .............. | A61B 17/1626 433/27 |

FOREIGN PATENT DOCUMENTS

| | | |
|---|---|---|
| CA | 2728008 A1 | 7/2012 |
| WO | 2012045455 A1 | 4/2012 |

* cited by examiner

*Primary Examiner* — Heidi M Eide
(74) *Attorney, Agent, or Firm* — Black McCuskey Souers & Arbaugh, LPA

(57) ABSTRACT

A reciprocating endodontic hand tool in which the torque applied to an instrument such as a debriding file can be set at or below an endurance limit of the file below which failure of the instrument will not occur. In preferred embodiments the tool can switch between settings in which the torque applied to the instrument is between the endurance limit of the file and an elastic limit of the file, by setting forward and reverse angles of rotation within specified limits. This reduces or eliminates opportunities for plastic distortion, fatigue and breakage of the file during the canal debriding/cleaning/shaping process in a root canal treatment or retreatment. In some embodiments the torque may be set to at or below a durability limit of the file below which failure of the instrument will not occur through repetitive strain over the course of a particular root canal treatment or retreatment.

7 Claims, 3 Drawing Sheets

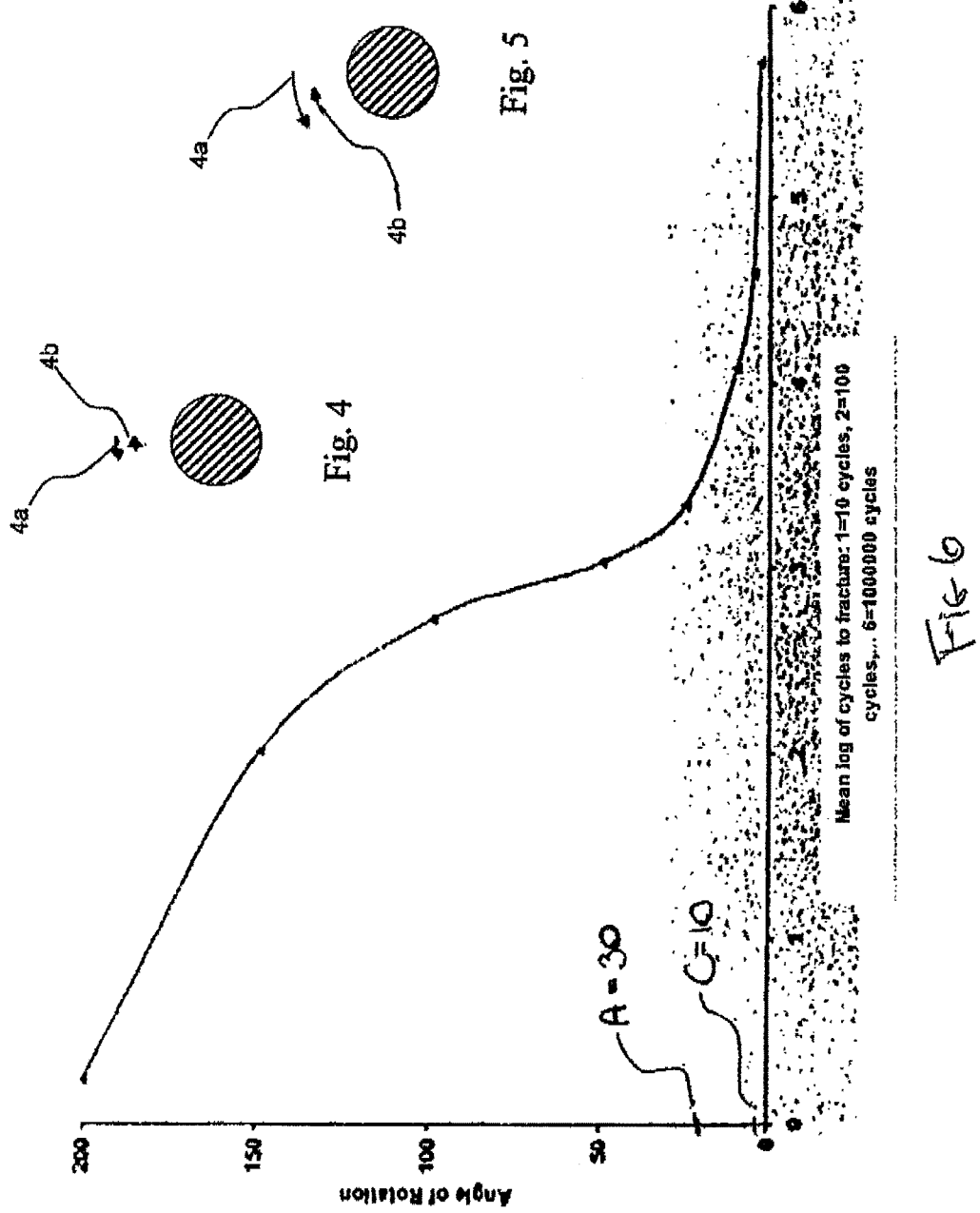

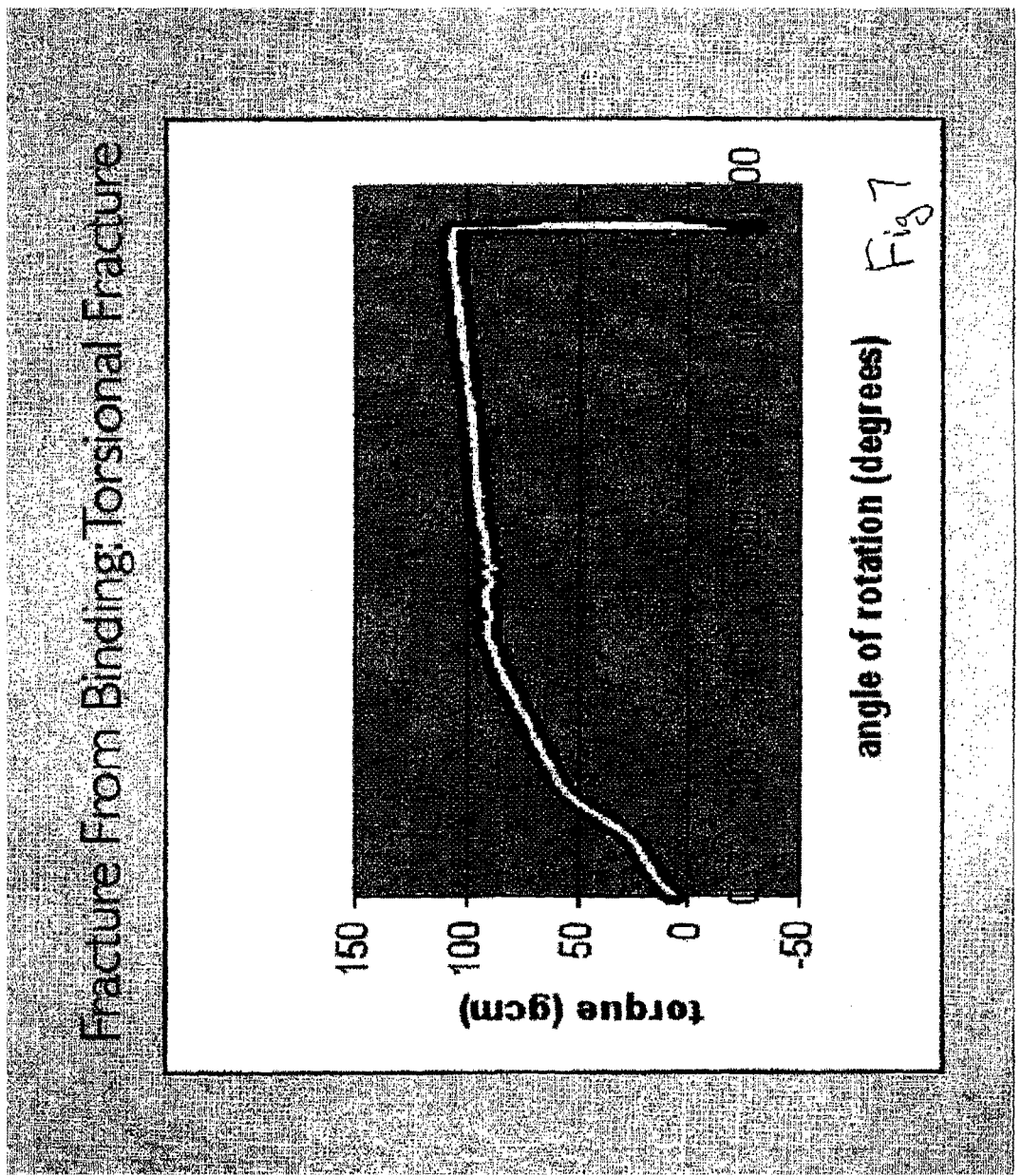

ENDODONTIC TOOL AND METHOD

FIELD OF THE INVENTION

This invention relates to endodontic tools.

BACKGROUND OF THE INVENTION

An important endodontic procedure, known as a "root canal" procedure, involves removing organic material from the root canals of an infected tooth and filling the canal with an inert obturating material such as gutta percha gum.

An effective root canal procedure avoids extraction of the infected tooth. In this procedure, a dentist or endodontist utilizes a series of endodontic instruments, for example files, for the debridement, cleaning and sterilization of the root canal. These files are rotated within the canal to clean the canal surfaces, removing debridement (organic) material in the process, facilitating improved irrigation, and in some cases shaping the canal for easier filling with the obturating material.

Root canal preparation, and root canal retreatment (to repair a defective root canal procedure), are typically effected by motor-driven instruments such as files. Root canal retreatment can be defined as a procedure to remove root canal filling materials from the tooth, followed by cleaning, shaping and obturating the canals.

Files used for debridement and removal of organic material, which are usually made of stainless steel or nickel titanium, or from modifications of stainless steel or nickel titanium, or from any other material or combination of materials which is generally rigid and allows the file to progress along the canal. Such files work like augers to move material out of the root canal via a helical groove. This effectively makes the file behave like a screw, driving forward when rotated in the forward direction (which may for example, depending upon the orientation of the threads, be the counter-clockwise direction) and backing off when rotated in the reverse (for example clockwise) direction. However, the threads defining the helical groove can lock or catch on interior canal surfaces, especially in constricted and/or curved parts of the canal. If too much force is applied to the file at such points the file can break, necessitating removal of the broken piece of file which can be a difficult procedure which could ultimately result in extraction of the tooth, effectively obviating the benefit of the root canal procedure, Motor-driven nickel-titanium files are widely used in a continuous rotation mode for the canal preparation. They offer significant advantages compared to hand-held instruments: they are faster, they make the procedure easier and therefore require a shorter learning curve, and they better maintain the canal curvature. However, instrument fracture, which can adversely affect the outcome of a root canal treatment, is a concern. When used in a continuous rotation mode, the instrument can bind in the canal. It will then be subjected to torsional stress, mainly at its tip. The dentist is typically not aware that the instrument is binding. The motor keeps rotating the instrument, and the torsional stress on the instrument will increase with the degree of rotation until a level high enough to fracture the instrument is reached. Instrument fracture will then occur. This is known as 'torsional fracture' or fracture from binding. Even without binding, the repeated torsional stress to which the instrument is subjected while engaging the canal walls and cutting tooth structure will in time cause fatigue of the instrument material, and instrument fracture from torsional fatigue will eventually occur.

The degree of rotation at which the instrument fractures is called the angle at fracture. The angle at fracture can be determined for any instrument, and at any part of the instrument. Usually it is measured at the tip of the instrument, which would be the portion of the instrument that most frequently binds in the canal during continuous rotation. Accordingly, a motor-driven tool has been developed which rotates through a defined arc "angle of rotation" in a 'forward' direction, which drives the file into the canal much like driving a screw, and a defined (typically lesser) arc of rotation in the "reverse" direction, which in like manner backs the file out of the canal. This reduces opportunities for the file to lock while effectively debriding, cleaning and shaping the root canal for filling. An example of such a tool, is described in U.S. Pat. No. 6,293,795 issued Sep. 25, 2001 to Johnson, which is incorporated herein by reference.

However, during the use of such tools the instrument will repeatedly engage dentine to cut it, and will therefore be repeatedly subjected to torsional stress. This will cause the file material, for example metal or plastic, to undergo structural changes. These changes can be reversible or irreversible, depending on the amount of torque to which the instrument is subjected during canal debridement and on the arc (angle) of rotation to which the instrument is subjected when engaging the tooth structure and binding in the canal. These structural changes will be irreversible if the torque on the instrument is higher than the elastic torque of the instrument (referred to herein as the "elastic limit"), for example when the instrument binds against the canal and the angle of rotation exceeds the elastic angle. In the tool described in U.S. Pat. No. 6,293,795, the torque set on the motor may be higher than the elastic limit of the file; thus, the arcs of rotation in the forward and/or reverse directions are capable of subjecting the file to a torque greater than its elastic limit. Under these conditions, any structural changes in the file material will be irreversible and through repeated use fracture from torsional fatigue, as described above, will eventually occur.

Recently, the use of motor-driven instruments in alternating clockwise and counter-clockwise reciprocation was introduced, to reduce the incidence of fracture from binding (torsional fracture) and fracture from torsional fatigue. An example is described in Yared G. Canal preparation using only one Ni—Ti rotary instrument: preliminary observations. Int Endod J 2008; 41: 339-44 published by the present applicant, which is incorporated herein by reference. Another example is described in U.S. patent publication no. 20120225406 published Sep. 6, 2012 by the present applicant, which is incorporated herein by reference. In this invention, the instrument is rotated alternately in the forward and reverse directions, but the arcs of rotation do not exceed the "elastic angle", defined as the angle at which the elastic limit of the instrument is reached, which is lower than the angle at fracture. The values of the arcs of rotation, which are lower than the elastic angle, are entered by the operator of the motor. When the instrument reaches the preset arc value (limit) in one direction, the motor will reverse the rotation of the instrument through the arc of rotation in the other direction. Therefore, the instrument will not fracture from binding because the instrument will reverse direction before the instrument reaches an angle at which the instrument can fracture. Fracture from binding (torsional fracture) is therefore substantially eliminated.

Also, if the instrument binds in the canal but is rotated to an angle lower than the elastic angle, torsional fatigue is reduced and consequently fracture from torsional fatigue is reduced. However, these types of endodontic instruments, including new unused instruments, can have surface defects such as corrosion pits and porosities. The repeated cycles of tension and compression to which the instrument is subjected during the canal preparation can initiate cracks in these defects; the cracks will then propagate and eventually cause fracture (Parashos P, Gordon I, Messer H H. Factors influencing defects of rotary nickel- titanium endodontic instruments after clinical use. J Endod 2004; 30: 722-5, which is incorporated herein by reference).

In addition, such motorized tools and files (used in reciprocation to specific arcs of rotation), which are very efficient for non-complex canal situations, are not able to safely address many complex canal anatomies. Despite this fact, dentists are tempted to use motor-driven files with such hand-held motorized devices in reciprocation mode, to enlarge and/or prepare the canal and to address complex canal situations, because of the ease with which they prepare the canal in comparison to manual techniques. This may lead to complications developing. For example, the repeated forward and reverse rotation of the file which does not advance in the canal will subject the file to torsional stress that will accumulate in specific regions, resulting in torsional fatigue and eventually fracture of the file. The present applicant introduced a novel canal preparation technique for root canal treatments and retreatments: (Yared G, 2008; Yared G, 2010: http://endodonticcourses.com/cmsAdmin/uploads/RECIPROC-OL-Article.pdf, which is incorporated herein by reference). In this new concept, preferably a single motor-driven instrument is used in reciprocation mode for the entire canal preparation. Compared to traditional continuous rotation and reciprocation techniques, this novel technique has a shorter learning curve, is faster, and in the majority of the canals requires only one instrument (compared to numerous instruments with the traditional techniques). However, the concern of fracture caused by crack initiation and propagation, and by stress accumulation in complex canal situations, becomes more critical in canal preparation techniques advocating the use of a single motor-driven instrument in a reciprocating mode for the root canal treatment or retreatment procedure (Yared G, 2008; Yared G, 2010: http://endodonticcourses.com/cmsAdmin/uploads/RECIPROC-OL-Article.pdf, which is incorporated herein by reference), because the single instrument, replacing several instruments as used in conventional techniques, is subject to longer periods of torsional stress.

The conventional view is that angles of rotation near the elastic limit of the instrument, at least in the forward direction, are required in order to effectively cut the tooth material. Accordingly, conventional techniques present the risk of instrument fatigue and fracture, with attendant potential complications, as described above. Gambarini teaches "NiTi rotary instruments should be operated only in the superelastic field, a range between the martensite 'start' clinical stress values and the martensite 'end' clinical stress values, which is a safe and efficient load. Unfortunately, this range is very small and very difficult to determine (16) and this amount of torque might not be adequate for an efficient cutting action, which is strongly influenced by the flute design of the files . . . the elastic and fracture limits of NiTi rotary instruments and their cutting efficiency are obviously dependent on design, dimensions and taper. This means that the right torque values for each individual instrument must be suggested by the manufacturers in order to obtain optimum cutting performance while minimising risks of failure. Unfortunately, it is not an easy task to find such a good balance. As previously mentioned, in some cases predetermined values might be too low to ensure efficient cutting action of the rotary instruments." Gambarini also states "Theoretically, an instrument used with high torque is very active and negotiation of root canals is easier, even if the incidence of instrument locking and consequent separation would tend to increase. Whereas with low torque, the cutting efficiency would be reduced and instrument progression in the canal would be more difficult. In such cases, if clinicians tended to force the instruments apically, they would increase the chances of locking and separation." (Gambarini, G. Advantages And Disadvantages Of New Torque-Controlled Endodontic Motors And Low-Torque NiTi Rotary Instrumentation, Australian Endodontic Journal 27, No. 3 December, 2001, which is incorporated herein by reference).

Thompson tested ten instruments ate deflection angles of 360°, 270°, 252°, 216°, 180°, 162°, 144°, 126°, 108° and 90°, but did not consider the results for angles of rotation below 144°, stating "Deflection angles of 126°, 108° and 90° bad greater than 250 cycles to fracture, but during the pilot study, these deflection angles did not allow the instrument to cut and advance into the resin block so they were not included in the experimental groups." (Thompson, Neil M. Development of a novel canal preparation technique using the torsional fatigue profile of the ProTaper™ F2 rotary instrument, Library and Archives Canada (ISBN: 978-0-494-21105-2) 2006, which is incorporated herein by reference). Prior to the present invention, such angles of rotation were considered to be too low to be effective in a root canal treatment or retreatement.

BRIEF DESCRIPTION OF THE DRAWINGS

In drawings which illustrate by way of example only a preferred embodiment of the invention.

FIG. 4 is a diagrammatic view illustrating examples of forward and reverse rotational arcs at the endurance limit.

FIG. 5 is a diagrammatic view illustrating examples of forward and reverse rotational arcs at the durability limit.

FIG. 6 is a graph showing the endurance limit and durability limit of a sample instrument.

FIG. 7 is a graph showing the torque on an instrument when bound at the tip in relation to the angle of rotation of the instrument.

DETAILED DESCRIPTION OF THE INVENTION

Figure 2:
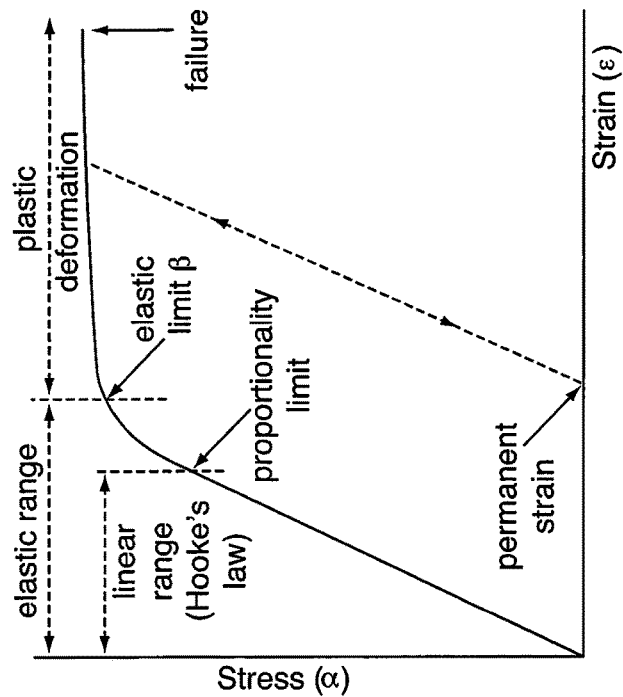
FIG. 2 is a graph showing the elastic limit of a sample instrument.

The present invention addresses these and other problems by providing a rotary tool 10 which can be set so that the torque on the instrument 2 (for example, a file) does not exceed the endurance limit torque C of the instrument 2 when the instrument binds or encounters substantial resistance in the canal. In some preferred embodiments the tool 10 can also be set so that the torque on the instrument 2 does not exceed the durability torque limit A, in the case of a complex canal structure in which the endurance limit torque C may not be effective, or the elastic torque limit B of the instrument 2 when the canal offers no substantial resistance to the instrument. In preferred embodiments the tool 10 may be switched between these settings according to the resistance encountered by the tool 10 against rotation of the instrument 2 and the efficacy of the instrument debriding the canal. The tool 10 is preferably set automatically to these respective limits in the conditions described, but alternatively may be set manually by the dentist or other practitioner.

The present invention thus provides a hand-held tool for rotating an endodontic instrument for preparing a root canal for filling in a root canal treatment or retreatment, the instrument having an elastic limit above which permanent deformation of the instrument will occur and an endurance limit below which failure of the instrument will not occur through repetitive strain, the tool comprising an instrument holder, a motor for applying a torque to the instrument holder and rotating the instrument holder through a selected arc of rotation alternately in each of forward and reverse directions, and a controller for controlling the rotation of the tool by applying a setting limiting each at least the forward arc of rotation to an angle at or below the endurance limit of the instrument where there is a substantial resistance against rotation of the instrument, whereby the instrument can cut the canal, remove material and advance in the canal.

The present invention further provides a hand-held tool for rotating an endodontic instrument for preparing a root canal for filling in a root canal treatment or retreatment, the instrument having an elastic limit above which permanent deformation of the instrument will occur and a durability limit below which failure of the instrument will not occur through repetitive strain over the course of a particular root canal treatment or retreatment, the tool comprising an instrument holder, a motor for applying a torque to the instrument holder and rotating the instrument holder through a selected arc of rotation alternately in each of forward and reverse directions, and a controller for controlling the rotation of the tool by applying a setting limiting each at least the forward arc of rotation to an angle at or below the durability limit of the instrument where there is a substantial resistance against rotation of the instrument, whereby the instrument can cut the canal, remove material and advance in the canal.

The present invention further provides a hand-held tool for rotating an endodontic instrument for preparing a root canal for filling in a root canal treatment or retreatment, the instrument having an elastic limit above which permanent deformation of the instrument will occur and a durability limit below which failure of the instrument will not occur through repetitive strain over the course of one particular root canal treatment or retreatment, the tool comprising an instrument holder, a motor for applying a torque to the instrument holder and rotating the instrument holder through a selected arc of rotation alternately in each of forward and reverse directions, and a controller for controlling the rotation of the tool by applying a setting limiting each at least the forward arc of rotation to an angle at or below the durability limit of the instrument where there is a substantial resistance against rotation of the instrument, whereby the instrument can cut the canal, remove material and advance in the canal.

The present invention further provides a method of rotating an endodontic instrument by a hand-held tool for preparing a root canal for filling in a root canal treatment or retreatment, the tool comprising an instrument holder for holding the instrument, a motor for rotating the instrument alternately in forward and reverse directions, and a control module for setting forward and reverse arcs of rotation of the instrument, the method comprising, in any order, the steps of: setting a limit on at least the forward arc of rotation to a rotational angle at or below a durability limit of the instrument below which failure of the instrument will not occur through repetitive strain over the course of a particular root canal treatment or retreatment, and activating the motor, whereby the instrument can cut the canal, remove material and advance in the canal.

Materials such as those used for debriding files have a quantifiable relationship between applied stress and the resulting strain on the material, which can be represented by a stress-strain curve such as that illustrated in FIG. 2. The slope of the stress-strain curve is constant over the region of elastic phase where applied stress does not cause permanent deformation. The plastic phase, where applied stress causes permanent deformation, starts just beyond the point corresponding to the elastic limit and the elastic angle on the slope of the stress-strain curve.

Figure 3:
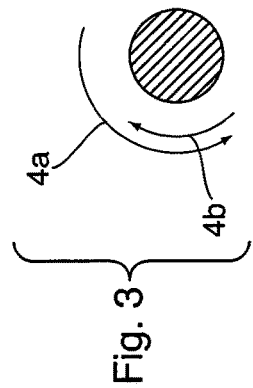
FIG. 3 is a diagrammatic view illustrating examples of forward and reverse rotational arcs at the elastic limit.

An instrument 2 experiences torsional stress when the canal offers a substantial resistance to rotation of the instrument 2. The elastic limit or elastic torque of the instrument 2 is defined herein as the maximum torsional stress that can be applied to a material without causing permanent deformation, and is in part based on the thickness, configuration and composition of the instrument 2. The elastic angle is defined herein as the strain or angle of rotation to which the instrument 2 is subjected at the elastic limit. Examples of the elastic limit and the elastic angle are shown in FIG. 3.

The endurance limit C of an instrument is in part based on the thickness, configuration and composition of the instrument 2, and also takes into account defects in the instrument 2. The endurance limit C, shown in FIG. 6, is defined herein as the maximum level of stress or strain to which the instrument 2 can be repeatedly subjected without failure, and can also be defined in terms of torsional stress (endurance limit torque) or in terms of strain (endurance limit angle, which is based on the rotational angle of the instrument 2). FIG. 7 for example illustrates the relationship of the torque applied to a NiTi instrument 2 relative to the angle of rotation when the instrument 2 binds in a canal such that the tip of the instrument 2 is rotationally fixed. The continued application of torque by the motor increases the torsional stress to around 80 gcm (gram-force centimetres) at one full rotation of the instrument, and at three full rotations exceeds 100 gcm which greatly exceeds the elastic limit of the instrument and ultimately reaches the failure point causing fracture to release the strain.

However, at or below the endurance limit C, continued cycling of the instrument 2 is unrestricted, will not decrease the strength of the material, and will not lead to failure of the instrument 2. The endurance limit C of the instrument is thus the level of stress or strain which a material can be subjected to repeatedly without permanent deformation. One test for example subjects the instrument 2 to repeated cycles (one cycle comprising loading the instrument with a stress or strain and releasing). The endurance limit is defined as the level of stress or strain to which the instrument can be cycled $10^6$ times without failure; at or below the endurance limit angle C, for example, a file or other instrument 2 would in theory have an infinite fatigue life, since torsional fatigue is eliminated; whereas above the endurance limit angle C the instrument 2 will eventually fail during the test. A typical endurance limit angle for a NiTi instrument 2 is about 10 degrees, as shown in FIG. 6 and schematically in FIG. 4 (not to scale). The durability limit angle may be different for instruments composed of other materials.

It has been discovered that, despite the very low angle of rotation at or below the endurance limit, the endurance limit angle C may be particularly advantageously used as the limit of the forward rotational angle in a number of root canal treatment and retreatment situations. For example, the endurance limit angle C may be advantageously used to eliminate torsional fatigue, stress accumulation, and crack initiation and propagation leading to instrument fracture when the dental practitioner bends the tip of the instrument 2 in order to search for the canal as the procedure is initiated—the precise direction and configuration of which can be difficult to ascertain in some patients—because of the increased likelihood of engaging tooth material during this part of the procedure. Bending the tip of instrument 2 for this procedure will cause a permanent defect in the instrument material and lower the fracture resistance of the instrument 2; therefore, the use of the endurance limit angle C as the upper limit of the forward rotation will generally eliminate the risk of instrument fracture.

For complex canal anatomies, the endurance limit angle C may be advantageously used throughout the root canal treatment or retreatment procedure. Alternatively, for simpler canal anatomies, the elastic angle or torque B may be employed as the forward rotational limit until the instrument 2 encounters a significant resistance in the canal, at which point the tool 10 can be switched either manually or automatically, for example to the endurance limit angle C, to continue the procedure, which the practitioner can complete with the confidence that the instrument 2 will not fracture.

In practice an instrument 2 will never be used through $10^6$ cycles, so as a practical matter the durability of an instrument 2 can be considered to be unlimited at or below the torsional strain or rotational point at which the instrument 2 has a fatigue life which will outlast a single root canal treatment or retreatment. This is defined herein as the "durability limit" A, shown by way of example in FIGS. 4 and 5. The durability limit A of an instrument is also in part based on the thickness, configuration and composition of the instrument 2, and takes into account defects in the instrument 2. Thus, the "durability limit" A is defined herein as the angle where an applied stress or strain causes failure (e.g. fracture) over a number of cycles that the instrument might be subjected to in practice during a single procedure. The durability limit A reflects the maximum level of stress (durability limit torque) or strain (durability limit angle, which referring to the rotational angle of the instrument 2) to which the instrument 2 can be repeatedly subjected without failure over the course of one particular root canal treatment or retreatment. At or below the durability limit A, continued cycling of the material is unrestricted, will not decrease the strength of the material any further, and will not lead to failure of the material over the course of a particular root canal treatment or retreatment. It has been determined that for a typical NiTi instrument 2 the durability limit angle A corresponds to a rotational angle of about 30 degrees, as shown schematically in FIG. 5 (not to scale). The durability limit angle may be different for instruments composed of other materials.

The slope of the stress-strain curve in FIG. 2 is constant over the region of elastic strain. Within this interval lies the "durability limit" A (shown in FIG. 6), at the maximum repetitive strain to which the instrument can be subjected without failure over the course of a particular procedure. As noted above, the point where applied stress causes the onset of permanent deformation is defined as the "elastic limit" B, as reflected by the change in the slope of the stress-strain curve. In the preferred embodiment the preset forward and reverse arcs of rotation of the instrument 2 should not subject the instrument 2 at any particular moment, or in any situation, to a torque (torsional stress) higher than the elastic limit B of the specific file 2 being used, regardless of the conditions encountered during the procedure. According to the invention, where the instrument 2 encounters resistance during the root canal procedure, the tool 10 can be switched, in some embodiments automatically, to a setting whereby the preset forward arc of rotation does not subject the instrument 2 to a torque higher than the durability limit A or endurance limit C of the specific file 2 being used, the preset reverse arc of rotation preferably not exceeding the preset forward arc of rotation.

In general throughout this description the elastic limit B, endurance limit C and durability limit A, and ranges related thereto, are referenced in terms of the rotational angle which results in a stress or strain when the tip of the instrument is rotationally fixed, for example binding against the canal wall. It will be appreciated by those skilled in the art that these limits and ranges also translate to specific torque values, referring to the torque applied by the tool 10 to the instrument 2 which in turn creates a stress or strain on the instrument 2 during use, the precise torque value being dependent upon the design and composition of the instrument 2.

The invention provides a tool 10 capable of controlling the forward and reverse angles of rotation to which it will subject the instrument 2 during reciprocation. In a preferred embodiment, in a normal canal anatomy where the instrument 2 does not encounter substantial resistance the tool 10 can be set so that the forward angle of rotation does not exceed the elastic limit angle B of the instrument 2, the reverse angle of rotation preferably not exceeding the forward angle of rotation. In a more complex canal anatomy where there is a substantial resistance against the rotation of the instrument 2, the forward angle of rotation can be set so that it does not exceed the endurance limit angle C of the instrument 2, depending upon the stage of the procedure and the complexity of the canal anatomy, the reverse angle of rotation preferably not exceeding the forward angle of rotation. In some situations the forward angle of rotation can be set so that it does not exceed the durability limit angle A of the instrument 2 (the reverse angle of rotation preferably not exceeding the forward angle of rotation), for part or all of the procedure, where for example the tip of the file 2 has been bent but no substantial resistance is encountered in all or part of the canal preparation procedure.

The preferred forward angle of rotation will thus depend on the complexity of the canal anatomy and the ease with which the file progresses in the canal; the reverse angle of rotation preferably will never exceed the forward angle of rotation. The tool 10 may be equipped with a torque sensor for sensing resistance against the instrument 2 and a controller which changes the angles of rotation automatically, depending on the degree of resistance against the instrument 2, or alternatively may be reset manually as required in response to conditions and/or resistance encountered during the root canal treatment or retreatment procedure. When the file 2 progresses easily in the canal, for example in a canal with a simple (relatively linear) anatomy, the forward angle of rotation in the preferred embodiment will preferably be no higher than the elastic angle B. However, in situations where the file 2 does not progress easily, for example in canals with a complex anatomy, or canals which are difficult to locate, the device of the invention allows the rotational angle values to be reduced to a level at or below the endurance limit angle C of the file 2, or where conditions permit, at or below the durability limit angle A of the file 2, the reverse angle of rotation preferably not exceeding the forward angle of rotation.

Automatic embodiments of the device 10 preferably allow the operator to use preset programmes (a) for simple canals (where the instrument 2 advances easily): the forward and reverse- arcs of rotation may be set closer to the angle at the elastic limit such that the torque does not exceed the elastic limit B; and (b) for canals with a complex anatomy: the forward and reverse arcs of rotation may be set at a level at or below an endurance limit C of the file, or at or below a durability limit A angle of the file, such that the torque does not exceed the endurance limit or durability limit, respectively, as selected by the practitioner.

The use of preset programme (b) for canals with a complex anatomy can be particularly advantageous. In abruptly curved canals, a file 2 driven in a continuous rotation or a reciprocation mode may hit the canal wall and be blocked at the point where the canal curvature starts, such that the file 2 will not advance any further into the canal. When this happens, complications may arise: the dentist may inadvertently fracture the file 2 in the canal, or block the canal with filing debris, while trying to make the file 2 advance along the curvature. These and other complications can adversely affect the outcome of the root canal treatment or retreatment.

In these complex canal situations, the dentist (or other dental practitioner) would conventionally use a hand-held file. The dentist conventionally forms a bend at the tip of the file, using pliers or a specially designed bending device. The file is then re-introduced into the canal. If the hand-held file tip hits the canal wall and is blocked, the dentist will drive the file manually with small right and left rotations until the bend in the file is oriented in generally the same direction as the curve of the canal; in that orientation, the tip of the file is not blocked by the canal wall, so the file can then be advanced into the canal with continued small left and right rotations. The bend created in the tip of the file is crucial to allowing the file to penetrate into the canal, at the point where the canal curvature starts.

Usually, this approach is reserved to hand held files. However, bending the tip of the file for this procedure will cause a permanent defect in the file material, which weakens the file and lowers its fracture resistance. In addition, with hand-held files this procedure involves an. increased risk of file fracture because the dentist cannot control with any precision the angle of rotation applied to the file, nor therefore the amount of torsional stress on the file, at the point of the curvature when the dentist abruptly encounters the canal wall. The weakened file may thus be subjected to sufficient torsional stress as to cause it to fracture. Similarly, fracture may occur if a file is being reciprocated to a severe enough angle that the file binds in the canal. Repeated clockwise and counterclockwise over-rotation of the file, or repeated submission of the file to stress levels that are not controlled by the practitioner, may cause torsional fatigue of the metal which can eventually lead to file fracture. In addition, due to the difficulty in negotiating such canals, the practitioner may be inclined to apply axial pressure on the file, which can also cause fracture and/or blockage of the canal.

In such abruptly curved canals, practitioners may be tempted to use a motor driven file 2 in reciprocating mode with specific arcs of rotation, after forming a bend at its tip in order to explore the canal and find its path. However, using conventional hand-held rotatable tools it will be difficult for the file 2 to align with the canal path because the angles of rotation are too large. Even if the reciprocating instrument 2 finds the canal path and is able to advance through the curvature, there remains an increased risk of fracture from fatigue (Cyclic fatigue testing of nickel-titanium endodontic instruments. Pruett J P, Clement D J, Carnes D L Jr. J Ended. 1997 Feb; 23(2):77-85, which is incorporated herein by reference), and crack initiation and propagation, especially since the bend in the file will have lowered its fracture resistance. The use of the preset programme (b) as described above to set the forward and reverse arcs of rotation at a level at or below the endurance limit angle C of the file, such that the torque does not exceed the endurance limit torque, will allow the file to find the canal path without the risk of fracture from binding or instrument fatigue (because the angles of rotation are very low). The forward and reverse arcs of rotation can each be set as low as 1 degree in order to allow an instrument 2 that is curved at its tip to find the canal path.

In the preferred embodiments the angle (arc) of rotation in one direction, usually the direction in which the file 2 will cut the dental structure (referred to herein as the "forward" direction), will typically be greater than the angle in the other ("reverse") direction. This facilitates progression of the file 2 along the canal. In some embodiments the tool 10 is set to a forward rotational angle at or below the elastic limit angle C for complex canals, but if the file 2 does not advance in the canal the forward rotational angle can be switched to at or below the durability limit angle A.

In some embodiments the tool 10 may optionally be equipped to control the speed of rotation of the file 2 in either direction, which may be set by the operator to depending on the on the complexity of the canal anatomy and the ease with which file 2 progresses in the canal. Conventionally the rotational speed of the instrument 2 will typically be reduced by the operator in situations where the file 2 does not progress easily along the canal, for example in canals with a complex anatomy, or when the file 2 stops from advancing in the canal. In a tool according to the invention, however, the rotational speed is advantageously increased when the device is switched to the endurance limit C (or, if desired for a particular procedure, the durability limit A), to make the procedure easier. This does not introduce any additional risk of file fatigue or fracture at the low rotational angles at or below the endurance and durability limits.

In some embodiments the tool 10 is preferably able to regulate the values of each of the torque, angles (arcs) of rotation, and speed, independently or simultaneously, depending on the resistance encountered by the file 2, which as noted above reflects the complexity of the canal anatomy and the ease with which file 2 progresses in the canal, such that the instrument 2 is able to cut the dental structure and safely advance in the canal. For example, where a torque sensor is provided in the tool 10 the torque can be limited, in addition to the inherent limits on the torque which can be applied within the forward and reverse rotational angles of the instrument 2. In this embodiment the tool 10 may be programmed with a torque limit that is below the torque experienced by the instrument 2 binding against the canal wall at the preset rotational limits, and reverse the rotation of the instrument where the preset torque limit is exceeded. This allows the instrument 2 to rotate to the full preset limit in each direction unless a resistance is encountered, in which case the instrument will only rotate to an angle at which the preset maximum torque is applied to the instrument 2.

It has thus been discovered that in cases of a complex anatomy the root canal procedure can be as just effectively accomplished using a reciprocating endodontic hand tool in which the angles of rotation applied to the debriding file 2 are at or below the endurance limit angle C, for example about 10 degrees, or the durability limit angle A of the file 2, for example about 30 degrees. This makes the root canal procedure or canal retreatment procedure safer, considerably reducing or potentially eliminating the possibilities of plastic distortion and fatigue, or breakage of the file 2 during the canal debriding/cleaning/shaping process, without reducing the efficacy of the procedure.

In a tool 10 according to the invention, instrument fatigue due to torsion (rotation) is virtually eliminated, because at the endurance limit C (or over the expected duration of a particular root canal procedure, the durability limit A) there is not sufficient physical degradation in the material of the instrument 2 to result in fracture of the instrument 2. However, in the preferred embodiment the forward and reverse rotational arcs 4a, 4b of the instrument 2 is also selected so that the torque on the file 2 does not at any time exceed the elastic limit B of the file 2. The lower the torque applied to the instrument 2 and the lower the forward and reverse arcs of rotations, the safer the root canal procedure or retreatment' procedure.

An endodontic tool 10 according to the invention thus comprises a handle 12 supporting a rotary head 14 providing an instrument holder such as a chuck 16 or other attachment means for inserting an instrument 2, such as a debriding file or similar endodontic instrument 2. The rotary head 14 may be rotated by any suitable means, including electric, pneumatic or hydraulic means, an electric motor being most commonly used as is known to those skilled in the art.

Figure 1:
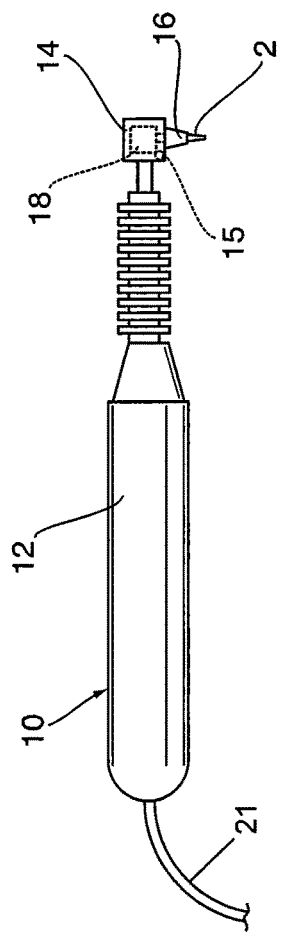
FIG. 1 is a diagrammatic view of an endodontic tool according to the invention.
Figure 1:
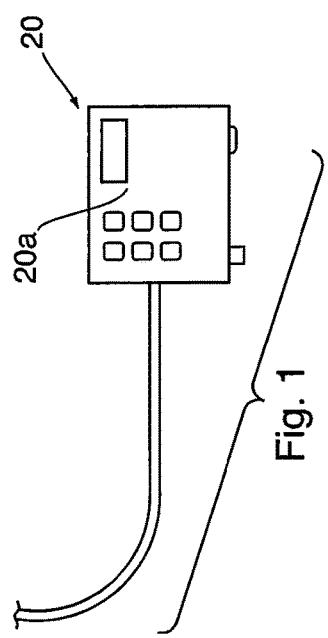

In the table-top version of the tool illustrated in FIG. 1, the handle 12 contains a motor controlled and powered via a power supply cord 21 attached to a control module 20. The motor drives the chuck 16 via a gear train 18 disposed within the rotary head 14. In alternate embodiments (not shown), without limitation, the rotary head may be attached to the motor and the motor connected by a cable to a dental chair system which rotates the motor by any suitable means, including electric, pneumatic or hydraulic means; the control module 20 can be disposed within or on the motor, or within or on the rotary head 14 or part of the dental chair system, for example in a battery-operated hand held device; or the rotary head 14 may provide means for setting the parameters electrically or mechanically. The invention is not limited to any particular configuration or arrangement of the tool 10, motor or drive means 18 used to drive the rotary head 14.

The control module 20 provides controls for the user of the tool 10 to set the arc of rotation of the instrument 2, and in some embodiments may also set such parameters as the speed, torque and others, for example as described in U.S. Pat. No. 6,293,795 which is incorporated herein by reference. An example of suitable reciprocating endodontic tools are the Endo EST Assistant, by GeoSoft (Russia) and Iendo Dual by Acteon.

A microprocessor (not shown) in a controller, for example control module 20, receives data from the user input into the control module user interface 20a to set the desired parameters for the forward and reverse arcs of rotation 4a, 4b of the reciprocating motion, a torque limit at which the motor will cease rotating in the current direction, and the rotational speed of the chuck 16 (which may differ in the forward and reverse directions).

According to one embodiment of the invention, the torque on the file 2 is set below the endurance limit C of the instrument 2, which may vary according to the composition and configuration of the instrument 2. In other embodiments the torque on the file 2 is set substantially at the elastic limit B of the instrument 2, which may also vary according to the composition and configuration of the instrument 2, when no substantial rotational resistance is encountered by the instrument 2; or during a particular procedure (for example, using a new file 2 where the file 2 is not intended to be re-used) may be set at or below the durability limit when substantial rotational resistance is encountered by the instrument 2.

The endurance limit C, durability limit A and elastic limit B of the instrument 2 can be determined by strain tests (in the present context the strain is directly related to the angle of rotation of the instrument 2), and may optionally be provided by the manufacturer of the instrument 2 on the packaging or literature accompanying the instrument 2. Ideally these limits are determined by measurements taken at about 1 mm from the tip of the instrument 2, however can be very difficult to test instruments 2 at this point because the tip of a file is very fine and tends to slip out of the gripping vice. Accordingly, measurements on endodontic instruments are usually taken at 2 to 3 mm from the tip, to determine for example torque at fracture, rotational angle at fracture, torque at permanent deformation, rotational angle at permanent deformation, and optionally other parameters. These measurements may also (or alternatively) be taken at different points along the instrument.

In use, the user (typically an endodontist or dentist) uses the user interface 20a of the control module 20 to set the limits of the forward and reverse rotational arcs 4a, 4b of the reciprocating motion, as shown schematically by way of example in FIG. 3 (not to scale), and in some embodiments the rotational speed (or speeds, which may differ) in the forward and reverse directions.

In embodiments which include a torque sensor, the user also sets the torque limit in the forward and reverse directions to be applied before the motor stops rotating in one direction and starts rotating in the opposite direction. In these embodiments the motor will stop rotating in the current direction (for example the forward direction) and start rotating in the opposite direction (for example the reverse direction) when either the preset limit of the arc of rotation is reached or when the preset torque limit is reached in the current direction. The torque sensor 15 in the head 14 delivers torque readings via the cable 21 to the control centre 20, which is programmed to arrest rotation (in the first direction, for example) of the chuck 16 and to reverse its direction of rotation when the programmed torque limit set for the first direction is reached. As noted herein, according to the present invention in these embodiments the preferred torque limit is set at a value not exceeding the elastic limit B of the instrument 2 in any situation, but switched so as to not exceed the endurance limit C (or durability limit A, for a particular procedure) at times when the instrument 2 is subjected to resistance during the root canal procedure.

Thus, according to the present invention the preferred arc of rotation in at least the forward direction set via the control centre 20 should be set substantially at the endurance limit angle C of the debriding file 2 for complex canal topologies. It has been discovered that this provides a safety advantage without reducing the efficacy of the root canal procedure. Preferably also the preferred arc of rotation in the reverse direction set via the control centre 20 should be set substantially at the endurance limit angle C of the debriding file 2 for complex canal topologies, however this is more for the efficacy of the procedure and less to avoid damage to the instrument 2, because in the reverse direction the instrument 2 is receding in the canal, not advancing.

The rotational arcs 4a, 4b in the forward and reverse directions may be the same, or the rotational arc limit in the forward direction 4a (referred to herein as the direction in which, due to the orientation of the helical thread, the thread of the file 2 will drive the file 2 deeper into the canal) may be less than the rotational arc limit in the reverse direction 4b; however, preferably the rotational arc limit in the forward direction 4a is greater than the rotational arc limit in the reverse direction 4b, as shown in FIG. 3. In the preferred embodiment where no substantial rotational resistance is encountered by the file 2, depending upon the design and composition of the file, the forward arc of rotation 4a may be set for example at about 140 to 160 degrees, most preferably about 150 degrees, corresponding substantially with the elastic limit angle B, and the normal reverse arc of rotation 4b (i.e. the rotational arc limit during normal operation of the tool 10 in the absence of excessive torque) may be for example set at about 20 to 90 degrees, most preferably around 30 degrees. In the preferred embodiment where substantial rotational resistance is encountered by the file 2, the forward arc of rotation 4a may be for example set at about 10 degrees or less, corresponding substantially with the endurance limit C, and the normal reverse arc of rotation 4b (i.e. the rotational arc limit during normal operation of the tool 10 in the absence of excessive torque) is preferably set at a lower angle than the forward arc of rotation. In either case, optionally a setting may be provided for a secondary reverse arc of rotation (not shown), which would be a different value (preferably lower) than the normal reverse arc of rotation 4b and which could be engaged when the forward rotational torque limit is exceeded before the preset forward arc angle limit is reached.

In most cases the endurance limit C can be used for the entire procedure. In certain limited cases the endurance limit C may be ineffective, such as where the canal is particularly difficult to navigate through (for example where the canal turns abruptly immediately below the crown). In these extreme cases, where the dentist or other practitioner determines it safe to do so (for example, when using a new file 2), the forward arc of rotation 4a can be set at up to about 30 degrees, corresponding substantially with the durability limit A, and the normal reverse arc of rotation 4b may be set at a lower angle than the forward arc of rotation.

As noted above, the invention can be advantageously applied to both root canal treatments and root canal retreatment. During a root canal treatment, the canals are cleaned and prepared to be filled. In some patients, a root canal treatment fails and an infection develops in the root canal. The infection has to be removed. One way to remove the infection that has developed in a tooth that already had a root canal treatment is to extract the tooth (which is a radical solution and to be avoided wherever possible), Another way is to re-do the root canal treatment, known as a root canal retreatment. This procedure can be done very efficiently and safely in the same manner described above. The instruments 2 are in this case used firstly to remove the filling from the root canal and then to re-prepare the canal to accept a new filling.

Conventionally root canal retreatment requires the use of solvents to soften the filling materials from the failed root canal procedure. The more effective solvents, for example chloroform, can be quite toxic and are banned in some jurisdictions. Less toxic solvents are available, but are less effective at dissolving the filling material, which makes the retreatment procedure more difficult. Also, conventional root canal retreatment involves clearing the root canal using an instrument rotated in a single direction. The procedure described herein, using a reciprocating tool and without the use of solvents, is safer and just as effective or more effective for root canal retreatment. It requires the use of a single instrument, and is an easier procedure to learn and to perform than conventional root canal retreatment procedures.

Various embodiments of the present invention having been thus described in detail by way of example, it will be apparent to those skilled in the art that variations and modifications may be made without departing from the invention. The invention includes all such variations and modifications as fall within the scope of the appended claims.

I claim:

1. A method comprising: using a hand-held tool for rotating an endodontic instrument for preparing a root canal for filling in a root canal treatment or retreatment procedure, the tool comprising an instrument holder, a motor for applying a torque to the instrument holder and rotating the instrument holder through a selected arc of rotation alternately in each of forward and reverse directions, and a controller for controlling the rotation of the tool by applying a setting limiting at least the forward arc of rotation to an angle not more than an endurance limit of the instrument of about 10 degrees where there is a substantial resistance against rotation of the instrument, the use comprising:
   a. inserting the instrument into the instrument holder,
   b. applying a torque to the instrument holder to rotate the instrument holder through a selected arc of rotation alternately in each of forward and reverse directions, and
   c. limiting at least the forward arc of rotation to a maximum angle of about 10 degrees during at least part of the procedure,
      whereby the instrument can cut the canal, remove material and advance in the canal.

2. The method of claim 1 wherein the step of limiting at least the forward arc of rotation to a maximum angle of about 10 degrees for substantially the entire procedure.

3. The method of claim 1 wherein the step of limiting at least the forward arc of rotation to a maximum angle of about 10 degrees when there is a substantial resistance against rotation of the instrument.

4. The method of claim 3 wherein in step c. a torque sensor measures a torque on the instrument holder to determine when there is a substantial resistance against rotation of the instrument.

5. The method of claim 1 further comprising a step of limiting the reverse arc of rotation to a maximum angle less than the angle of the forward arc of rotation.

6. The method of claim 1 further comprising a step of setting a speed of rotation independently of the arc of rotation.

7. The method of claim 1 further comprising a step of setting the torque independently of the arc of rotation.

* * * * *